United States Patent [19]

Hen

[11] Patent Number: 4,855,526
[45] Date of Patent: Aug. 8, 1989

[54] PROCESS FOR PREPARING ETHYLENE-HIGHER OLEFIN COPOLYMER OILS WITH ZIEGLER-NATTA CATALYST IN MIXED ALIPHATIC-AROMATIC SOLVENT

[75] Inventor: John Hen, Skillman, N.J.

[73] Assignee: Mobil Oil Corporation, New York, N.Y.

[21] Appl. No.: 134,645

[22] Filed: Dec. 18, 1987

[51] Int. Cl.$^4$ ............................................. C07C 2/02
[52] U.S. Cl. .................................................. 585/524
[58] Field of Search ....................................... 585/524

[56] References Cited

U.S. PATENT DOCUMENTS

| | | |
|---|---|---|
| 2,907,805 | 10/1959 | Bestian et al. . |
| 2,993,942 | 7/1961 | White et al. . |
| 3,676,521 | 7/1972 | Stearns et al. . |
| 3,923,919 | 12/1975 | Stearns et al. . |
| 3,981,941 | 9/1976 | Butter ................................. 585/524 |
| 4,305,920 | 12/1981 | Hasuo et al. ...................... 585/524 |
| 4,451,688 | 5/1984 | Kuroda et al. .................... 585/524 |
| 4,486,615 | 12/1984 | Langer, Jr. . |

FOREIGN PATENT DOCUMENTS 874577  8/1961  United Kingdom ................ 585/524

OTHER PUBLICATIONS

A. W. Langer, Jr., *Linear Alpha–Olefins by Catalytic Oligomerization of Ethylene*, J. Macromol. Sci.–Chem., A4(4), pp. 775–787, Jul. 1970.

H. Höcker et al, *Polymerization of Ethylene with Soluble Ziegler–Natta Catalysts*, Die Makromolekulare Chemie (1971), pp. 107–118.

*Primary Examiner*—Curtis R. Davis
*Attorney, Agent, or Firm*—Alexander J. McKillop; Charles J. Speciale; Stanislaus Aksman

[57] ABSTRACT

Low viscosity copolymers of ethylene and higher olefins are prepared with Ziegler-Natta catalysts in the presence of an aliphatic-aromatic solvent mixture, e.g., 1:1 (by volume) of hexane:toluene. The copolymerization can be conducted without hydrogen and subsequent cracking or dewaxing steps are not necessary to obtain oils with high VI and low pour point suitable for use as basestocks, blendstocks and as shear stable VI improvers.

34 Claims, No Drawings

PROCESS FOR PREPARING ETHYLENE-HIGHER OLEFIN COPOLYMER OILS WITH ZIEGLER-NATTA CATALYST IN MIXED ALIPHATIC-AROMATIC SOLVENT

BACKGROUND OF THE INVENTION

It is known that ethylene can be oligomerized to form low molecular weight oils, intermediate weight waxes or semisolids or polymerized to form high molecular weight polymers using Ziegler-Natta catalysts, i.e., a transition metal compound in combination with an alkyl metal halide. Catalysts in which the transition metal is titanium in compounds such as titanium tetrachloride, and in which the alkyl metal halide is an aluminum compound, such as an ethyl aluminum chloride, have been successfully used to prepare a variety of olefin oligomers and polymers. However, it is difficult to obtain oligomers of ethylene and higher olefins such as propylene which are suitable for lubricating oils directly without the use of hydrogen in the reaction or the necessity of thermal cracking to remove waxy components.

The preparation of ethylene-propylene copolymer oils using Ziegler-Natta catalysts is disclosed in U.S. Pat. No. 3,676,521 which is incorporated herein by reference. The patent explains that a synthetic lubricant desirably has maximum pour point of 0° F. ($-18°$ C.), a minimum viscosity index (VI) of 110 and a viscosity at 210° F. (99° C.) of 1 to 60 cs. The patent also discloses the difficulty of achieving these characteristics without a cracking step which is necessary unless high hydrogen pressure of 500 to 1000 psig is used to control molecular weight. The reaction is conducted in an inert solvent such as hexane, although the solvent can be omitted by using excess propylene as the solvent.

The oligomerization of ethylene alone with an alkyl aluminum halide-titanium halide catalyst, in the presence of inert solvent which includes at least 40 volume percent of a halogenated aromatic hydrocarbon and optionally a diluent such as heptane, benzene, or xylene is disclosed in U.S. Pat. No. 2,993,942. The patent discloses that ethylene is unique to the invention in that other olefins do not respond to give similar products.

In accordance with this invention mixed aliphatic-aromatic solvents are used to prepare ethylene-propylene oligomers having high VI and low pour point, with Ziegler-Natta catalysts under low hydrogen pressure or in the absence of hydrogen.

SUMMARY OF THE INVENTION

Low viscosity oligomers of ethylene and higher olefins are prepared using a Ziegler-Natta catalyst in the presence of a mixture of solvents including an aliphatic solvent and a more hydrophilic aromatic solvent in a volume ratio of 0.2:1 to 5:1.

The presence of the hydrophilic solvent assists in producing lower molecular weight products so that low viscosity oils having a high VI (viscosity index) and low pour point can be produced with little or no hydrogen and without the necessity of cracking or other treatment to reduce the wax content.

DETAILED DESCRIPTION OF THE INVENTION

In a typical reaction, a closed reactor, such as an autoclave, is charged with the mixed solvent. The reactor is then pressured with hydrogen (if it is used) to a desired pressure; then with the higher olefins, e.g., propylene, and ethylene to desired pressures. Charging of the catalyst components can be accomplished in a variety of ways, but customarily the reaction is not initiated until after the original charge of reactants. Since the reaction is somewhat exothermic, means for the control of temperature conditions are preferably provided for affording reasonably constant reaction temperatures. Reaction temperatures between 0°–125° C. are suitable, with 15°–55° C. preferred.

Hydrogen at low pressures below 100 psig may be optionally used to further control molecular weight but is not necessary in the practice of this invention.

After the reaction has proceeded to a desired extent, the catalyst is deactivated by any suitable means, e.g., by addition of an alkanol such as isopropanol, and the copolymer recovered, such as by known methods, including removal of catalyst residues.

The reaction is conducted in a mixed solvent system of an aliphatic solvent and an aromatic solvent in a volume ratio of about 1:5 to 5:1, e.g., about 1:1. The aliphatic solvent is preferably an alkane such as heptane or hexane. The aromatic solvent can be a halogenated solvent. Toluene, xylene and chlorobenzene are preferred aromatic solvents.

Particularly suitable Ziegler catalysts have an aluminum component and a titanium component. The preferred aluminum component has the formula $RAlX_2$, $R_3Al_2X_3$ or $R_2AlX$ in which R is an alkyl group with 1 to 6 carbon atoms, and X is a halide, preferably chloride. The preferred titanium compounds have the formula $TiCl_4$, $TiRCl_3$, $TiR_4$, $Ti(OR)Cl_3$, $Ti(OR)_2Cl_2$, $Ti(OR)_3Cl$ in which R is an alkyl of 1 to 6 carbon atoms.

Generally the molar ratio of Al/Ti is less than or equal to 3, preferably 0.5 to 2.5.

The resulting ethylene-propylene copolymer oils are useful as lubricants without the necessity of use of hydrogen or thermal cracking to lower molecular weight. These oils have excellent viscosity indices from 100 to greater than 170, pour points as low as $-48°$ C., and have desirable properties as synthetic lubricant basestocks or blendstocks. Although ethylene propylene copolymers are preferred, other alpha-olefin copolymers or terpolymers with ethylene can be prepared under the specified conditions. Carbon numbers for the alpha olefins can range from 2 to 20.

The invention is illustrated by the following non-limiting examples in which all parts are by weight unless otherwise specified.

COMPARATIVE EXAMPLE 400 ml of hexane stored in 4A-molecular sieve and purged of its oxygen content with dry nitrogen was charged into a previously inerted 1 liter stainless steel autoclave reactor. The temperature of the reactor contents was held constant at 20° C. (+ or $-2°$ C.) throughout the reaction. After degassing with dry nitrogen, 12 milli-moles of $TiCl_4$ as a 10% w/v solution in hexane and 18 meq of ethyl-aluminum sesquichloride (as a 25% solution in hexane) were charged consecutively at an Al/Ti ratio of 1.5/1.0. Dry hydrogen gas (50 psig) was added and the flow of hydrogen was stopped. A continuous feed at constant monomer molar ratio of 0.78/1 ethylene to propylene was maintained for 110 minutes at which time the unreacted gases were vented and the reaction quenched with isopropanol. After extracting the catalyst residues with several isopropanol/water extracts, the hexane solution was filtered through a bed of Celite filter aid and another bed of sodium sulfate. After stripping of solvent by rotary evaporation, 99.6 grams of crude product was recovered. The light ends boiling below 90° C. at 0.03 mm Hg (or the below 650° F. fraction) was removed from the crude product by vacuum distillation to yield 89% topped oil with 114 cs (at 110° C.) kinematic viscosity, 148 VI and −19° C. pour point. The topped oil is a random copolymer with a 64% ethylene composition.

EXAMPLE I

The Comparative Example was followed except a more polar solvent blend of 1/1 volume ratio of toluene and hexane was employed. This modification of solvent produced a dramatic change in the properties of the topped oil. Kinematic viscosity was reduced to 10.4 cs (at 100° C.), pour point to −45° C. with lower VI of 102. The topped oil has a slightly higher ethylene content at 68%.

EXAMPLE 2

Example 1 was repeated except that hexane was replaced with heptane and hydrogen was not employed. The resulting topped oil was clear, with a kinematic viscosity of 18 cs at 100° C., VI of 116 and a pour point of −41° C. The (GPC) number average molecular weight of this topped oil is 580 using polystyrene molecular weight standards. The ethylene content in the copolymer was 65%.

EXAMPLES 3–5

The Comparative Example was modified by using a 1/1 volume blend of hexane/toluene, eliminating use of hydrogen and using varying Al/Ti mole ratio from 0.75 (Example 4), 1.5 (Example 3) to 2.25 (Example 5). The effect of higher Al/Ti mole ratio is to increase the propagation rate relative to termination rate, resulting in higher molecular weight and viscosity. The results are summarized in Table I which show useful lubricants are obtainable by modifying Al/Ti ratio.

TABLE I

| Example | 4 | 3 | 5 |
| --- | --- | --- | --- |
| Al/Ti mole ratio | 0.75 | 1.5 | 2.25 |
| Cs at 100° C. | 8.8 | 18 | 63 |
| VI | 94 | 116 | 146 |
| Mn | 480 | 580 | 1000 |
| Pour Point (°C.) | −48 | −41 | −28 |

EXAMPLES 6–8

This series of experiments probed the influence of the monomer feed ratio starting fom $C_2/C_3$ of 0.78/1 (Example 4), to 1.28/1 (Example 6), 2.0/1 (Example 7), and 4.4/1 (Example 8) while keeping the following conditions constant: Al/Ti=0.75/1, no hydrogen, 20° C., 1/1 volume blend of hexane/toluene as solvent. The results as summarized in Table II indicate that low viscosity copolymer oils with VI of 151 can be obtained at the highest ethylene feed (Example 7). These examples indicate that highly useful lubricant compositions can be prepared from the copolymers of this invention.

TABLE II

| Example | 4 | 6 | 7 | 8 |
| --- | --- | --- | --- | --- |
| $C_2/C_3$ mole feed | 0.78 | 1.28 | 2.0 | 4.4 |
| Cs 100° C. | 8.8 | 7.6 | 12.6 | 11.1 |
| VI | 94 | 118 | 137 | 151 |
| Mn | 480 | 470 | 570 | 570 |
| Pour Point (°C.) | −48 | −48 | −38 | −39 |

I claim:

1. A process for preparing a copolymer oil of ethylene and higher alpha-olefin containing at least 20 mole percent ethylene comprising copolymerizing ethylene and said higher alpha-olefin in the presence of an Al-Ti Ziegler-Natta catalyst in which the Al/Ti molar ratio is 3 or less, and a mixture of an aliphatic solvent and an aromatic solvent in a volume ratio of 1:5 to 5:1, to obtain a copolymer oil having a VI of at least 100 and a point below −17.8° C. without cracking or dewaxing said oil.

2. The process of claim 1 in which said higher alpha-olefin is propylene.

3. The process of claim 1 in which said Ziegler-Natta catalyst comprises an aluminum compound which is $RAlX_2$, $R_3Al_2X_3$, or $R_2AlX$, and a titanium compound which is $TiCl_4$, $TiRCl_3$, $TiR_4$, $Ti(OR)Cl_3$, $Ti(OR)_2Cl_2$, $Ti(OR_3)Cl$ or $Ti(OR)_4$ where X is a halide and R is alkyl of 1 to 6 carbon atoms.

4. The process of claim 2 in which said Ziegler-Natta catalyst comprises an aluminum compound which is $RAlX_2$, $R_3Al_2X_3$, or $R_2AlX$, and a titanium compound which is $TiCl_4$, $TiRCl_3$, $TiR_4$, $Ti(OR)Cl_3$, $Ti(OR)_2Cl_2$, $Ti(OR)_3Cl$ or $Ti(OR)_4$ where X is a halide and R is alkyl of 1 to 6 carbon atoms.

5. The process of claim 1 in which said aliphatic solvent is hexane or heptane and said aromatic solvent is toluene, xylene or chlorobenzene.

6. The process of claim 2 in which said aliphatic solvent is hexane or heptane and said aromatic solvent is toluene, xylene or chlorobenzene.

7. The process of claim 3 in which said aliphatic solvent is hexane or heptane and said aromatic solvent is toluene, xylene or chlorobenzene.

8. The process of claim 4 in which said aliphatic solvent is hexane or heptane and said aromatic solvent is toluene, xylene or chlorobenzene.

9. The process of claim 1 in which the volume ratio of said aliphatic solvent to said aromatic solvent is 1:2 to 2:1.

10. The process of claim 2 in which the volume ratio of said aliphatic solvent to said aromatic solvent is 1:2 to 2:1.

11. The process of claim 3 in which the volume ratio of said aliphatic solvent to said aromatic solvent is 1:2 to 2:1.

12. The process of claim 4 in which the volume ratio of said aliphatic solvent to said aromatic solvent is 1:2 to 2:1.

13. The process of claim 5 in which the volume ratio of said aliphatic solvent to said aromatic solvent is 1:2 to 2:1.

14. The process of claim 6 in which the volume ratio of said aliphatic solvent to said aromatic solvent is 1:2 to 2:1.

15. The process of claim 7 in which the volume ratio of said aliphatic solvent to said aromatic solvent is 1:2 to 2:1.

16. The process of claim 8 in which the volume ratio of said aliphatic solvent to said aromatic solvent is 1:2 to 2:1.

17. The process of claim 3 in which said aluminum compound is $R_3Al_2X_3$, the titanium compound is $TiCl_4$ and R is ethyl.

18. The process of claim 7 in which said aluminum compound is $R_3Al_2X_3$, the titanium compound is $TiCl_4$ and R is ethyl.

19. The process of claim 11 in which said aluminum compound is $R_3Al_2X_3$, the titanium compound is $TiCl_4$ and R is ethyl.

20. The process of claim 17 in which said higher alpha-olefin is propylene.

21. The process of claim 18 in which said higher alpha-olefin is propylene.

22. The process of claim 19 in which said higher alpha-olefin is propylene.

23. The process of claim 20 in which the volume ratio of said aliphatic solvent to said aromatic solvent is 1:1.

24. The process of claim 21 in which the volume ratio of said aliphatic solvent to said aromatic solvent is 1:1.

25. The process of claim 22 in which the volume ratio of said aliphatic solvent to said aromatic solvent is 1:1.

26. The process of claim 23 in which X is Cl.

27. The process of claim 24 in which X is Cl.

28. The process of claim 25 in which X is Cl.

29. The process of claim 26 in which added hydrogen is used at pressures of 0 to 100 psig.

30. The process of claim 29 in which no added hydrogen is used.

31. The process of claim 27 in which hydrogen is used at pressures of 0 to 100 psig.

32. The process of claim 31 in which no added hydrogen is used.

33. The process of claim 28 in which no added hydrogen is used at pressures of 0 to 100 psig.

34. The process of claim 33 in which no added hydrogen is used.

* * * * *